US006790997B2

(12) United States Patent
Eckert et al.

(10) Patent No.: US 6,790,997 B2
(45) Date of Patent: Sep. 14, 2004

(54) PREPARATION OF CARBONYL COMPOUNDS FROM ALCOHOLS

(75) Inventors: Markus Eckert, Köln (DE); Hans-Christian Militzer, Odenthal (DE); Matthias Beller, Rostock (DE); Christian Döbler, Lichtenhagen-Dorf (DE); Gerald Mehltretter, Ontario (CA); Uta Sundermeier, Rostock (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/201,732

(22) Filed: Jul. 23, 2002

(65) Prior Publication Data

US 2003/0055291 A1 Mar. 20, 2003

(30) Foreign Application Priority Data

Jul. 26, 2001 (DE) ......................................... 101 37 455

(51) Int. Cl.[7] .................. C07C 45/38; C07C 45/39; C07C 45/56; C07C 45/59
(52) U.S. Cl. .................. 568/320; 549/71; 549/484; 568/322; 568/339; 568/360; 568/402; 568/426; 568/431
(58) Field of Search ................ 568/320, 339, 568/360, 402, 431, 322, 426; 549/71, 484

(56) References Cited

U.S. PATENT DOCUMENTS 4,306,083 A  12/1981  Ma ............................ 568/432

OTHER PUBLICATIONS

Coleman et al. 'Catalytic Oxidation of Alcohols into Aldehydes and Ketones by an Osmium–Copper Bifunctional System using Molecular Oxygen' Tetrahedron Letters, 40 (1999) 3723–3726.*

Somaiah P V Et Al: "Kinetics of Oxidation of alcohols, diols and alpha–hydroxy acids by osium (VIII) in aqueous alkaline medium: evidence in support of hydride ion abstraction mechanism" Indian Journal of Chemistry, Section A, Bd. 27A, Nr. 10, 1988, Seiten 876–879, XP008012564 das ganze Dokument.

Chemical Abstracts, vol. 108, No. 17, Apr. 25, 1988 Columbus, Ohio, US; abstract No. 149742z, Somaiah P V Et Al: "Role of osmium tetroxide in oxidation of 2–propanol in presence and absence of different one– and two–equivalent oxidants in aqueous alkaline medium" Seite 674; XP002227272 Zusammenfassung & Indian J. Chem., Sect. A, Bd. 26A, Nr. 5, 1987, Seiten 402–406.

Chemical Abstracts, vol. 99, No. 25, Dec. 19, 1983 Columbus, Ohio, US; abstract No. 211922j, Naidu H M K Et Al: Kinetics and mechanism of Osmium(VIII) and ruthenium(III) catalyzed oxidation of ethanediol and 1, 2–propanediol with chloramine–T in alkaline and acid media Seite 592; XP002227273 Zusammenfassung & Z. Phys. Chem. (Leipzig), Bd. 264, Nr. 3, 1983, Seiten 469–480.

Maione A M Et Al: "Carbonyl compounds by 1–10 osmium tetroxide oxidation: preferential oxidation of primary over secondary hydroxy groups" Synthesis, Nr. 11, Nov. 1984, Seiten 955–957, XP002175379 das ganze Dokument.

Tetrahedron Letters, 40, (month unavailable) 1999, pp. 3723–3726, "Catalytic Oxidation of Alcohols into Aldehydes and Ketones by an Osmium–Copper Bifunctional System using Molecular Oxgen,", Karl S. Coleman, Maurice Coppe, Christophe Thomas, and John A. Osborn.

* cited by examiner

*Primary Examiner*—Peter O'Sullivan
(74) *Attorney, Agent, or Firm*—Godfried R. Akorli; Diderico van Eyl; Jill Denesvich

(57) ABSTRACT

The invention relates to a process for the preparation of carbonyl compounds by the oxidation of alcohols in the presence of osmium compounds as catalysts in water or a solvent mixture containing water.

10 Claims, No Drawings

PREPARATION OF CARBONYL COMPOUNDS FROM ALCOHOLS

BACKGROUND OF THE INVENTION

The present invention relates to a novel process for the preparation of carbonyl compounds by oxidation of alcohols in the presence of catalysts based on osmium compounds.

Aldehydes and ketones are important carbonyl compounds, which find use as chemical intermediates, particularly as fine chemicals, and also as precursors for dyes, medicaments, and active ingredients for agro-chemicals.

Although the literature already discloses a large number of preparative processes for aldehydes and ketones, there is great interest in new environmentally friendly catalytic synthesis methods because of the variety of differing carbonyl compounds of industrial interest. For example, hydroformylation of olefins, the formylation of aromatics, the ozonolysis of olefins, and the oxidation of alcohols are applied industrially to the synthesis of aldehydes. Of the synthetic processes mentioned, the oxidation of alcohols is particularly interesting for fine chemical syntheses. The availability and price of alcohols make them ideal starting materials for aldehyde and ketone syntheses. Oxidations of alcohols to carbonyl compounds succeed in the presence of stoichiometric amounts of chromium compounds using dimethyl sulfoxide/oxalyl chloride, periodate, manganese dioxide or other reagents. From an ecological, but also economic standpoint, processes employing cost-effective oxidizing agents, such as hydrogen peroxide with sodium hypochlorite in the presence of catalysts, are more interesting. However, catalytic processes employing oxygen as the oxidizing agent are even more advantageous. The literature discloses metal-catalyzed oxidations of alcohols using oxygen, which in most cases employ ruthenium and palladium catalysts. In general, only alcohols having allylic or benzoic structure are converted with good yields, although it is disadvantageous that relatively high catalyst concentrations are necessary, long reaction times are required, or cocatalysts must be added. The prior art processes require catalyst quantities that are too high for industrial application. The quantity of the noble metal catalyst that is used dominates the raw material costs of the reactions and makes the corresponding processes uneconomical. Furthermore, it is difficult to separate noble metal traces from the product if >1 mol % of catalyst is used. However, this is a requirement for application of the process in the field of pharmaceutical and agrochemical intermediate production.

Osmium-catalyzed alcohol oxidations have hardly been investigated up to now. The oxidation of predominantly allylic and benzylic primary alcohols in the system $OsO_4$ (1 mol %)/CuCl (1.5 mol %) in toluene at 100° C. with oxygen and with the addition of molecular sieves has been described; results between 19 and 96% were achieved at high selectivity (cf. K. S. Coleman, M. Coppe, C. Thomas, J. A. Osborn, *Tetrahedron Lett.*, 40, 3723 (1999)). The oxidation of 4-methoxybenzalcohol to 4-methoxybenzaldehyde using oxygen and 1 mol % $OsO_4$ in toluene at 100° C. in the presence of molecular sieves is also described. However, it is pointed out that leaving out CuCl leads to a reduction in the catalyst activity.

The need therefore exists for a novel, industrially operable process for the preparation of carbonyl compounds that is cost-effective, requires low quantities of metal catalysts, and facilitates a high catalyst productivity.

Surprisingly, a process for the preparation of carbonyl compounds by oxidation of alcohols in the presence of osmium compounds is found to fulfil the above-recited conditions and additionally delivers the carbonyl compounds in high purity and yield.

SUMMARY OF THE INVENTION

The present invention provides a process for the preparation of carbonyl compounds of the formula (I)

where
R and $R^1$ are independently hydrogen or an alkyl, cycloalkyl, aryl, or heteroaryl radical, each of which is optionally substituted, or
R and $R^1$ combine with the carbon atom to which they are bonded to form a cycloalkyl radical,
comprising reacting alcohols of the general formula (II)

where R and $R^1$ are as defined above for formula (I), with an oxidizing agent in the presence of a catalytic quantity of an osmium compound in water or a solvent mixture containing water at a pH of from 7 to 14.

DETAILED DESCRIPTION OF THE INVENTION

When R and $R^1$ as defined above are alkyl, they generally represent a straight-chain or branched hydrocarbon radical having from 1 to 18 carbon atoms that is optionally substituted by from 1 to 8 identical or different substituents. Alkyl preferably represents a straight-chain or branched hydrocarbon radical having from 1 to 8 carbon atoms, which is optionally substituted by from 1 to 3 identical or different substituents. More preferably, alkyl represents methyl, ethyl, and octyl.

Where R and $R^1$ as defined above are cycloalkyl, they generally represent a cyclic hydrocarbon radical having from 5 to 18 carbon atoms that is optionally substituted by from 1 to 8 identical or different substituents and in which one or more $CH_2$ groups of the cycloalkyl radical can be replaced by heteroatoms (preferably N, O, or S). Suitable cycloalkyl radicals R or $R^1$ in which one or more $CH_2$ groups of the cycloalkyl radical are replaced by one or more heteroatoms (preferably N, O, or S) are a piperadine or piperazine radical. The cycloalkyl radical preferably contains from 5 to 10 carbon atoms (more preferably cyclohexyl) in which again one or more $CH_2$ groups of the cycloalkyl radical can be replaced by one or more heteroatoms (preferably N, O, or S).

When R and $R^1$ as defined above are aryl, they generally represent an aromatic radical having from 6 to 14 carbon atoms (preferably from 6 to 10 carbon atoms) that is optionally substituted by from 1 to 8 identical or different substituents and is optionally fused (particularly phenyl or naphthyl that is optionally substituted by from 1 to 3 identical or different substituents, preferably phenyl, p-methylphenyl, or p-methoxyphenyl).

When R and R¹ as defined above are heteroaryl, they generally represent an aromatic radical having from 4 to 14 carbon atoms (preferably from 5 to 10 carbon atoms, particularly from 5 to 7 carbon atoms) and from 1 to 3 (preferably 1 or 2) heteroatoms selected from the group consisting of N, O, and S that is optionally substituted by from 1 to 8 identical or different substituents and is optionally fused (most preferably furan or thiophene).

Said alkyl, cycloalkyl, aryl, or heteroaryl radicals are each optionally substituted by from 1 to 8 identical or different substituents selected from the group consisting of alkyl, CN, COOH, COO-alkyl, COO-aryl, CO-alkyl, CO-aryl, O-alkyl, O-aryl, O—CO-aryl, O—CO-alkyl, OCOO-alkyl, $N(alkyl)_2$, NH-alkyl, $N(aryl)_2$, NH-aryl, NO, $NO_2$, NOH, aryl, fluorine, chlorine, bromine, iodine, $NO_2$, $Si(alkyl)_3$, CHO, $SO_3H$, $SO_3$-alkyl, $SO_2$-alkyl, SO-alkyl, $CF_3$, NHCO-alkyl, $CONH_2$, CONH-alkyl, NHCOH, NHCOO-alkyl, $CHCHCO_2$-alkyl, $CHCHCO_2H$, $PO(aryl)_2$, $PO(alkyl)_2$, $PO_3H_2$, and $PO(O-alkyl)_2$, where the alkyl and aryl radicals again have the general and preferred meanings given above.

Particularly suitable alcohols of the formula (II) for the preparation of carbonyl compounds of the formula (I) are those in which at least one of the radicals R or R¹ represents an aryl or heteroaryl group as defined above.

The compounds of the formula (II) can be used individually or in any desired mixture.

The process of the invention is carried out in the presence of water as solvent. A two-phase solvent system is generally formed with the alcohol of the formula (II). In principle, additional organic solvent can be added as well as the alcohol of the formula (II). From 1 to 5 l/mol (preferably from 2 to 3 l/mol) of the alcohol of the formula (II) are usually used. Suitable additional solvents include inert organic solvents, such as aliphatic ethers, aromatic or aliphatic hydrocarbons, tertiary alcohols and esters, halogenated hydrocarbons, dipolar aprotic solvents such as dialkyl sulfoxides, N,N-dialkylamides of aliphatic carboxylic acids, and also their mixtures. Preference is given to tertiary alcohols, esters, and ethers.

The process of the invention is carried out at a pH value in the range from 7 to 14, preferably from 9 to 10, very preferably from 10 to 11. An aqueous solution having a pH value in the range from 7 to 14 is generally used as the aqueous phase. The basic pH value of the solution is achieved by addition of a base to water. It is generally advantageous to work in buffered aqueous solutions, preferably at a pH from 9 to 13. The basic pH value is set by addition of known buffers to water or by titration of a base into the reaction mixture. Occasionally, it can be advantageous for the removal of the carbonyl compounds for an aqueous salt solution or buffered aqueous salt solution (for example, an aqueous solution of an alkali or alkaline earth metal halide) to be used as solvent in place of water or buffered aqueous solutions.

All customarily used oxidizing agents are generally suitable for the operation of the process of the invention. Preference is given to molecular oxygen or a gas mixture comprising molecular oxygen or to alkali or alkaline earth metal hypochlorite solutions.

Preferred gas mixtures are those that contain at least 15% by volume of oxygen. Air and gas mixtures having an oxygen content of >15% are more preferred.

The aqueous alkali metal hypochlorite solutions are preferably those of sodium hypochlorite. More preferably, this aqueous sodium hypochlorite solution has an NaOCl concentration in the range from 1 to 16% by weight, particularly from 3 to 12% by weight.

The reaction is preferably carried out at temperatures of from 20 to 200° C. In many cases, it has proved worthwhile to work at temperatures of from 30 to 150° C., preferably from 40 to 120° C.

The process of the invention can be carried out at atmospheric pressure, e.g., by passing oxygen through the reaction solution. However, it is advantageous for the reaction rate when oxygen overpressure is employed. The process can be operated at pressures of up to 200 bar, but it is customary to work at a pressure of 60 bar only and preferable to work in the range from atmospheric pressure to 20 bar.

The selectivity of the oxidation reaction and the productivity and activity of the catalyst can sometimes be improved by the addition of amine ligands. Suitable amine ligands include, for example, pyridines, bipyridines, quinolines, quinuclidine derivatives, DABCO, and quinine and quinidine ligands.

The osmium catalysts are generally one or more different osmium compounds in the oxidation states +8 and +6. However, it is also possible to use osmium precatalysts in lower oxidation states. These precatalysts are converted under the reaction conditions into catalytically active Os(VIII) species. Suitable osmium catalysts or catalyst precursors can include, for example, one or more of the following: $OsO_4$, $K_2Os_2(OH)_4$, $Na_2Os_2(OH)_4$, $Os_3(CO)_{12}$, $OsCl_3$, $H_2OsCl_6$, $[CF_3SO_3Os(NH_3)_5](O_3SCF_3)_2$, $OsO_4$ on vinylpyridine, and $Bu^tNOsO_3$.

In the process of the invention, osmium catalyst is used in catalytic quantities relative to the alcohol (II). In general, from 0.02 to 0.00001 equivalent (preferably from 0.01 to 0.0001 equivalent and more preferably from 0.008 to 0.0005 equivalent), based on the alcohol (II), is used.

The amine ligand is customarily used in a quantity of from 1:1 to 100:1 (based on Os). However, the reaction also succeeds in principle without any ligand being present.

The reaction times for the process of the invention are in general from 8 to 24 h and depend on the substrate and catalyst concentration.

In principle, the reaction is carried out by adding the osmium catalyst and optionally the ligand to the buffered aqueous solution with stirring. After addition of the alcohol to be oxidized, the oxidizing agent (e.g., hypochlorite solution) is introduced. When oxygen is used as a reoxidizing agent, the reaction vessel after purging is connected to a leveling vessel filled with oxygen or an elevated pressure of oxygen or air is applied in the pressure vessel. The reaction solution is stirred for from 12 to 24 h and is extracted with acetic acid after the addition of sodium sulfite, and the content of oxidation product and unconverted alcohol in the organic phase is determined by means of gas chromatography (GC).

The particular advantage of the process of the invention is the use of oxygen or oxygen-containing gases as reoxidizing agents in the presence of only very small quantities of osmium catalyst. Surprisingly, high yields of aldehyde or ketone are achieved despite low quantities of osmium. This can be attributed to the high selectivity and reactivity of the catalyst system.

Catalyst productivity can be further enhanced by again admixing the aqueous catalyst phase once refreshed with alcohol (II). In this way, the catalyst costs for the process of the invention are minimized, so that industrial processes can be operated economically.

The particular advantages of the novel process reside in the price advantage of the oxidizing agent, the simplicity of operation, and the high catalyst productivity compared to oxidation reactions of alcohols disclosed in the literature. The catalyst productivities (turnover numbers) achieved in the process of the invention of up to 20,000 are remarkable.

The carbonyl compounds prepared according to the invention can be used, inter alia, as precursors for dyes, agrochemicals, cosmetics, and pharmaceuticals.

The following examples serve to elucidate the process of the invention, without restricting it either in spirit or scope. Those skilled in the art will readily understand that known variations of the conditions of the following procedures can be used. Unless otherwise noted, all temperatures are degrees Celsius and all percentages are percentages by weight.

EXAMPLES

Example 1

3.7 mg of $K_2OsO_4.2H_2O$ (0.01 mmol) were weighed into a Schlenk vessel. 25 ml of a buffer solution of pH 10.4 prepared from 0.5 molar $K_2HPO_4$ solution and 2 molar NaOH and also 10 ml of 2-methyl-2-propanol were added with stirring by means of a magnetic stirrer. Two phases formed. The vessel was warmed in a water bath at 50° C. and purged with oxygen. After addition of 206 µl of benzyl alcohol (2 mmol), the reaction vessel was connected to a burette filled with oxygen, and the reaction solution was stirred for 18 hours at 50° C. under a small $O_2$ pressure (about 50 cm water column).

The mixture was worked up as follows: About 1 g of sodium bisulfite and 20 ml of acetic acid were added to the reaction solution. After stirring for 10 minutes, the upper organic phase was separated off. Benzaldehyde and also unconverted alcohol were determined by GC. Yield of benzaldehyde 85% (selectivity 85%)

Example 2

Example 1 was repeated, except that 0.03 mmol of 1,4-diaza-bicyclo[2,2,2]octane (DABCO) was added to the osmium salt. Yield of benzaldehyde: 87% (selectivity 87%)

Example 3

Example 2 was repeated, except that the reaction time was 16 hours. Yield of benzaldehyde: 93% (selectivity 93%)

Example 4

Example 2 was repeated, except that toluene was used instead of 2-methyl-2-propanol and the reaction time was 24 hours. Yield of benzaldehyde: 89% (selectivity 97%)

Example 5

Example 2 was repeated, except that 276 mg (2 mmol) of 4-meth-oxybenzyl alcohol were reacted over a reaction time of 22 hours. Yield of anisaldehyde: 92% (selectivity 92%)

Example 6

Example 2 was repeated, except that 242 µl (2 mmol) of 1-phenyl-ethanol were reacted over a reaction time of 12 hours. Yield of acetophenone: 95% (selectivity 95%)

Example 7

Example 6 was repeated, except that 276 µl (2 mmol) of 1-(p-toluyl)ethanol were reacted. Yield of p-methylacetophenone: 93% (selectivity 93%)

Example 8

Example 2 was repeated, except that 282 µl (2 mmol) of p-methoxy-α-methylbenzyl alcohol were reacted over a reaction time of 21 hours. Yield of p-methoxyacetophenone: 92% (selectivity 92%)

Example 9

Example 2 was repeated, except that 2 mmol of 3-(hydroxy-methyl)thiophene were reacted over a reaction time of 19 hours. Yield of thiophen-3-carboxaldehyde: 80% (selectivity 80%)

Example 10

Example 2 was repeated, except that 2 mmol of 1-(2-furyl)ethanol were reacted over 24 hours. Yield of 2-furyl methyl ketone: 85% (selectivity 91%)

Example 11

Example 2 was repeated, except that 2 mmol of (-)-borneol ((-):(+) ratio of 96:4) were reacted over 20 hours. Yield of camphor (sum of the enantiomers): 97% (selectivity 97%)

Example 12

Example 2 was repeated, except that 265 µl (2 mmol) of cyclo-octanol were reacted at 80° C. for 24 hours. Yield of cyclooctanone: 71% (selectivity 93%)

Example 13

Example 12 was repeated, except that 317 µl of (2 mmol) of 2-octanol were reacted. Yield of 2-octanone: 49% (selectivity 93%)

Example 14

Example 2 was repeated, except that 428 mg of (2 mmol) of hydrobenzoin were reacted for 16 hours. Yield of benzaldehyde: 91% (selectivity 91%)

Example 15

Example 14 was repeated, except that 428 mg (2 mmol) of meso-hydrobenzoin were reacted at 80° C. for 18 hours. Yield of benzaldehyde: 92% (selectivity 92%)

Example 16

A pressure autoclave fitted with a Teflon stirrer was charged with 0.0004 mmol of $K_2OsO_4.2H_2O$ (0.2 ml of freshly prepared solution of 7.4 mg of $K_2OsO_4.2H_2O$ in 10 ml water), 0.0012 mmol of DABCO (0.2 ml of a freshly prepared solution of 6.8 mg in 10 ml of water), 25 ml of a buffer solution of pH 10.4 prepared from 0.5 molar $K_2HPO_4$ solution and 2 molar NaOH, and also 12 ml of 2-methyl-2-propanol. After addition of 412 µl (4 mmol) of benzyl alcohol, a pressure of 20 bar air was applied and the autoclave heated to 80° C. After stirring for 24 hours at 80° C., the vessel was cooled and depressurized. 200 mg sodium bisulfite were added, the mixture was extracted twice with 20 ml acetic acid each time, and the contents of benzyl alcohol and benzaldehyde were determined by gas chromatography. Yield of benzaldehyde: 90% (selectivity 92%)

Example 17

Example 16 was repeated, except that 4 mmol of benzyl alcohol in the presence of 0.0002 mmol of $K_2OsO_4.2H_2O$/0.0012 mmol of DABCO were reacted at 100° C. at a pressure of 40 bar air for 24 hours. Yield of benzaldehyde: 86% (selectivity 94%)

Example 18

Example 16 was repeated, except that 4 mmol of phenylethanol were reacted. Yield of acetophenone: 83% (selectivity 91%)

Example 19

Example 17 was repeated, except that 4 mmol of phenylethanol were reacted. Yield of acetophenone: 75% (selectivity 92%)

Example 20

A Schlenk vessel was charged with 3.7 mg of $K_2OsO_4.2H_2O$ (0.01 mmol). 25 ml of a buffer solution of pH 10.4 prepared from 0.5 molar $K_2HPO_4$ solution and 2 molar NaOH, 4 ml of a 3% sodium hypochlorite solution, and also 10 ml of 2-methyl-2-propanol were added. After addition of 265 µl (2 mmol) of cyclooctanol, the mixture was stirred for 24 hours in a liquid bath at 70° C. 20 ml of acetic acid were added to the reaction solution. After stirring for 10 minutes, the upper organic phase was separated off. Cyclooctanone and unconverted alcohol were determined by means of GC. Yield of cyclooctanone: 56% (selectivity 80%)

Example 21

Example 20 was repeated, except that 2 mmol 1-phenylethanol were reacted at 50° C. for 24 hours with 0.004 mmol of $K_2OsO_4.2H_2O$ (2 ml of a freshly prepared solution of 7.4 mg of $K_2OsO_4.2H_2O$ in 10 ml water) and 10 ml of hypochlorite solution. Yield of acetophenone: 74% (selectivity 80%)

Example 22

Example 21 was repeated, except that 2 mmol of benzyl alcohol were reacted at 25° C. for 24 hours. Yield of benzaldehyde: 95% (selectivity 97%)

Example 23

Example 20 was repeated, except that 2 mmol of benzyl alcohol were reacted at 50° C. for 24 h with 0.001 mmol of $K_2OsO_4.2H_2O$ (0.5 ml of a freshly prepared solution of 7.4 mg of $K_2OsO_4.2H_2O$ in 10 ml water) and 10 ml hypochlorite solution. Yield of benzaldehyde: 88% (selectivity 90%)

What is claimed is:

1. A process for the preparation of a carbonyl compound of the formula (I)

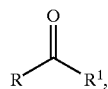

where
R and $R^1$ are independently hydrogen or an alkyl, cycloakyl, aryl or heteroaryl radical, each of which is optionally substituted, or
R and $R^1$ combine with the carbon atom to which they are bonded to form a cycloalkyl radical, comprising reacting an alcohol of the formula (II)

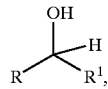

where R and $R^1$ are as defined above for formula (I), with an oxidizing agent in the presence of a catalytic quantity of an osmium compound in water or a solvent mixture containing water at a pH of from 7 to 14, wherein the oxidizing agent is molecular oxygen or a gas mixture comprising molecular oxygen, or alkali or alkaline earth metal hypochlorite solutions.

2. A process according to claim 1 wherein in the alcohol of the formula (II) at least one of R and $R^1$ represents an aryl or heteroaryl group.

3. A process according to claim 1 wherein in the alcohol of the formula (II) R and $R^1$ independently represent hydrogen, straight-chain or branched $C_1$–$C_8$-alkyl that is optionally substituted by from 1 to 3 identical or different substituents, $C_5$–$C_{10}$-cycloalkyl that is optionally substituted by from 1 to 3 identical or different substituents, substituted phenyl or naphthyl that is optionally substituted by from 1 to 8 identical or different substituents, or $C_5$–$C_7$-heteroaryl that is optionally substituted by from 1 to 3 identical or different substituents and has 1 or 2 heteroatoms selected from the group consisting of N, O, and S, or R and $R^1$ together with the carbon atom to which they are bonded represent $C_5$–$C_{10}$ cycloalkyl that is optionally substituted by from 1 to 3 identical or different substituents.

4. A process according to claim 1 to wherein the oxidizing agent is oxygen or a gas mixture comprising at least 15% by volume of oxygen.

5. A process according to claim 1 wherein the solvent mixture is a mixture of water and at least one organic solvent selected from the group consisting of aliphatic ethers, aromatic or aliphatic hydrocarbons, tertiary alcohols and esters, halogenated hydrocarbons, and dipolar aprotic solvents.

6. A process according to claim 1 wherein at least one osmium compound selected from the group consisting of $OsO_4$, $K_2Os_2(OH)_4$, $Na_2Os_2(OH)_4$, $Os_3(CO)_{12}$, $OsCl_3$, $H_2OsCl_6$, $[CF_3SO_3Os(NH_3)_5](O_3SCF_3)_2$, $OsO_4$ on vinylpyridine, and $Bu^tNOsO_3$ is used as a catalyst and/or a precatalyst.

7. A process according to claim 1 wherein the quantity of the osmium compound is in the range from 0.02 to 0.00001 equivalent based on the alcohol of formula (II).

8. A process according to claim 1 carried out at a temperature of from 20 to 200° C.

9. A process according to claim 1 carried out at a pressure of up to 200 bar.

10. A process according to claim 1 wherein at least one amine ligand is added as a cocatalyst.

* * * * *